United States Patent [19]
Moll et al.

[11] Patent Number: 5,817,003
[45] Date of Patent: *Oct. 6, 1998

[54] CONTROLLER FOR A PATIENT WARMING DEVICE

[75] Inventors: Robert G. Moll, Loveland; Michael M. Donnelly, Cincinnati, both of Ohio; Alan Gutwillig, Appleton, Wis.

[73] Assignee: Hill-Rom, Inc., Batesville, Ind.

[*] Notice: The term of this patent shall not extend beyond the expiration date of Pat. No. 5,453,077.

[21] Appl. No.: 533,371

[22] Filed: Sep. 25, 1995

Related U.S. Application Data

[63] Continuation-in-part of Ser. No. 169,675, Dec. 17, 1993, Pat. No. 5,453,077.

[51] Int. Cl.⁶ ................................................ A61G 11/00
[52] U.S. Cl. ................................................ 600/22; 128/736
[58] Field of Search ........................ 600/21–22; 128/736

[56] References Cited

U.S. PATENT DOCUMENTS

| | | |
|---|---|---|
| 3,158,150 | 11/1964 | Croasdaile . |
| 3,335,713 | 8/1967 | Grosholz et al. . |
| 3,387,600 | 6/1968 | Terzian . |
| 3,511,162 | 5/1970 | Truhan . |
| 3,618,734 | 11/1971 | Khan . |
| 3,776,217 | 12/1973 | van Galen et al. . |
| 3,782,362 | 1/1974 | Puzio . |
| 3,821,947 | 7/1974 | Schossow . |
| 3,858,570 | 1/1975 | Beld et al. . |
| 4,063,495 | 12/1977 | Duvlis . |
| 4,140,105 | 2/1979 | Duvlis . |
| 4,321,913 | 3/1982 | Maluta et al. . |
| 4,361,137 | 11/1982 | Grosholz . |
| 4,423,669 | 1/1984 | Bullock et al. . |
| 4,617,912 | 10/1986 | Beer et al. . |
| 4,750,474 | 6/1988 | Dukhan et al. . |
| 4,809,677 | 3/1989 | Mackin et al. . |
| 4,846,783 | 7/1989 | Koch et al. . |
| 4,936,824 | 6/1990 | Koch et al. . |
| 5,162,038 | 11/1992 | Wilker . |
| 5,285,519 | 2/1994 | Barsky et al. .............................. 600/22 |
| 5,308,310 | 5/1994 | Roff et al. . |
| 5,316,542 | 5/1994 | Koch et al. ................................ 600/22 |
| 5,453,077 | 9/1995 | Donnelly et al. .......................... 600/22 |

FOREIGN PATENT DOCUMENTS

| | | |
|---|---|---|
| 0236851 | 2/1987 | European Pat. Off. . |
| 2031559 | 11/1970 | France . |
| 2061704 | 7/1979 | Germany . |
| 3607575 | 9/1987 | Germany . |
| 122184 | 11/1974 | Japan . |
| 2175213 | 11/1986 | United Kingdom . |
| 90/09771 | 9/1990 | WIPO . |

OTHER PUBLICATIONS

12/71 Journal of Pediatrics "Air Curtain Incubator for use in a Intensive–Care Nursery", Musch, Adams and Sunshine, vol. 79, No. 6, pp. 1024–1030.
INFA–CARE 2000 brochure, Infa–Care, Inc., 1972.

*Primary Examiner*—John P. Lacyk
*Attorney, Agent, or Firm*—Barnes & Thornburg

[57] ABSTRACT

A patient warming apparatus includes a support surface for supporting a patient, a convective heater for supplying convective heat to warm the patient, and a radiant heater for supplying radiant heat to warm the patient. The apparatus also includes a controller having a first output coupled to the convective heater and a second output coupled to the radiant heater for varying output power levels of the convective heater and the radiant heater, respectively, to maintain the patient located on the support surface at substantially a preselected temperature.

29 Claims, 9 Drawing Sheets

CONTROLLER FOR A PATIENT WARMING DEVICE

RELATED APPLICATION

This application is a continuation-in-part of application Ser. No. 08/169,675, filed Dec. 17, 1993, now U.S. Pat. No. 5,453,077, the specification of which is expressly incorporated by reference.

BACKGROUND AND SUMMARY OF THE INVENTION

The present invention relates to a support for patients and particularly to a patient thermal support device that provides an elevated and protected support surface for a patient and that protects and minimizes the disruption of the environment immediately surrounding the patient. More particularly, the present invention relates to a controller that is configured to warm a patient using both convective and radiant warming techniques.

Incubators and radiant warmers have both been used to maintain the appropriate body temperature of small or premature patients. An incubator provides a generally transparent enclosure within which heated air is circulated to minimize the heat loss of the patient. More specifically, heat is transferred to the patient via convective heat transfer. Incubators are typically provided with a large access door to allow for placement or removal of the patient in the incubator as well as supplemental access ways such as hand ports or small entry doors to permit routine care of the patient while minimizing heat loss from the incubator and the patient.

Radiant warmers provide for continuous and open access to a patient to accommodate a high frequency of intervention by the caregiver. Radiant warmers transfer heat to the patient via radiant heat transfer, typically from infrared heaters which emit infrared energy that is absorbed by the patient. The infrared heater is typically mounted to a stationary support which is suspended above the patient support surface of the radiant warmer. Radiant warmers typically include no canopies or other enclosures that are commonly available on patient support devices to minimize the evaporative water losses of patients because such canopies or enclosures might obstruct the caregiver's access to the patient.

Patients can suffer from conditions that render it desirable to minimize contact between the patient's skin and objects, even including objects such as blankets. In addition, it is occasionally necessary for caregivers to have constant and ready access to the patient in certain critical care situations. The present invention provides a controller to control a convective heater, a radiant heater, and a humidifier to control prescribed environment for the patient while providing for continuous and open access to a patient.

According to one aspect of the present invention, a patient warming apparatus includes a support surface for supporting a patient, a convective heater for supplying convective heat to warm the patient, and a radiant heater for supplying radiant heat to warm the patient. The apparatus also includes a controller having a first output coupled to the convective heater and a second output coupled to the radiant heater for varying output power levels of the convective heater and the radiant heater, respectively, to maintain the patient located on the support surface at substantially a preselected temperature.

The apparatus further includes a temperature sensor having an output coupled to the controller to provide feedback to the controller. An input device is coupled to the controller to permit a caregiver to adjust the preselected or desired temperature. The apparatus includes an alarm coupled to the controller. The controller generates an alarm signal if the output from the temperature sensor changes by a predetermined level.

In the illustrated embodiment, the apparatus also includes a humidifier for adding moisture to air adjacent the support surface. A humidity sensor has an output coupled to the controller. The controller has a third output coupled to the humidifier to adjust the humidifier based on the output from the humidity sensor and to maintain the humidity at substantially a preselected level.

Also in the illustrated embodiment, the apparatus further includes an air curtain generator for providing at least one air curtain over the support surface to create a controlled patient space. The apparatus includes a canopy for supporting the radiant heater which is movable relative to the support surface between an up position spaced apart from the support surface and a down position located in close proximity to the support surface. A position indicator is provided for generating an output signal related to a distance between the radiant heater and the support surface. The position indicator is coupled to the controller to permit the controller to adjust the output power level of the radiant heater based upon said distance.

In one control arrangement, the controller activates only the convective heater until an output power level of the convective heater exceeds an upper limit, at which point the controller activates the radiant heater. The controller continues to increase the output power level of the radiant heater until the output power level of the convective heater drops below the upper limit. The controller reduces the output power level of the radiant heater when the output power level of the convective heater drops below a lower limit.

According to another aspect of the present invention, an apparatus is provided controlling operation of a patient warming device which includes a support surface for supporting a patient, a convective heater for supplying convective heat to warm the patient, a radiant heater for supplying radiant heat to warm the patient, and a humidifier for adding moisture to air adjacent the support surface. The apparatus includes a controller having a first output coupled to the convective heater and a second output coupled to the radiant heater for varying output power levels of the convective heater and the radiant heater, respectively, to maintain the patient located on the support surface at substantially a preselected temperature. The controller has a third output coupled to the humidifier to adjust an output from the humidifier. The apparatus also includes a temperature sensor having an output coupled to the controller to provide feedback to the controller so that the controller maintains the patient located on the support surface at substantially the preselected temperature. The apparatus further includes a humidity sensor having an output coupled to the controller. The controller adjusts the humidifier based on the output from the humidity sensor to permit the controller to maintain the humidity at substantially a preselected level.

In one illustrated embodiment, the temperature sensor is configured to be coupled to the patient. The apparatus includes an alarm coupled to the controller. The controller generating an alarm signal if the output from the temperature sensor changes above or below a predetermined level from the preselected or desired temperature. The apparatus further includes an input device coupled to the controller to permit a caregiver to adjust the preselected temperature and the preselected humidity level.

Additional objects, features and advantages of the invention will become apparent to those skilled in the art upon consideration of the following detailed description of preferred embodiments exemplifying the best mode of carrying out the invention as presently perceived.

BRIEF DESCRIPTION OF THE DRAWINGS

The detailed description refers particularly to the accompanying drawing figures in which.

DETAILED DESCRIPTION OF THE DRAWINGS

Figure 1:
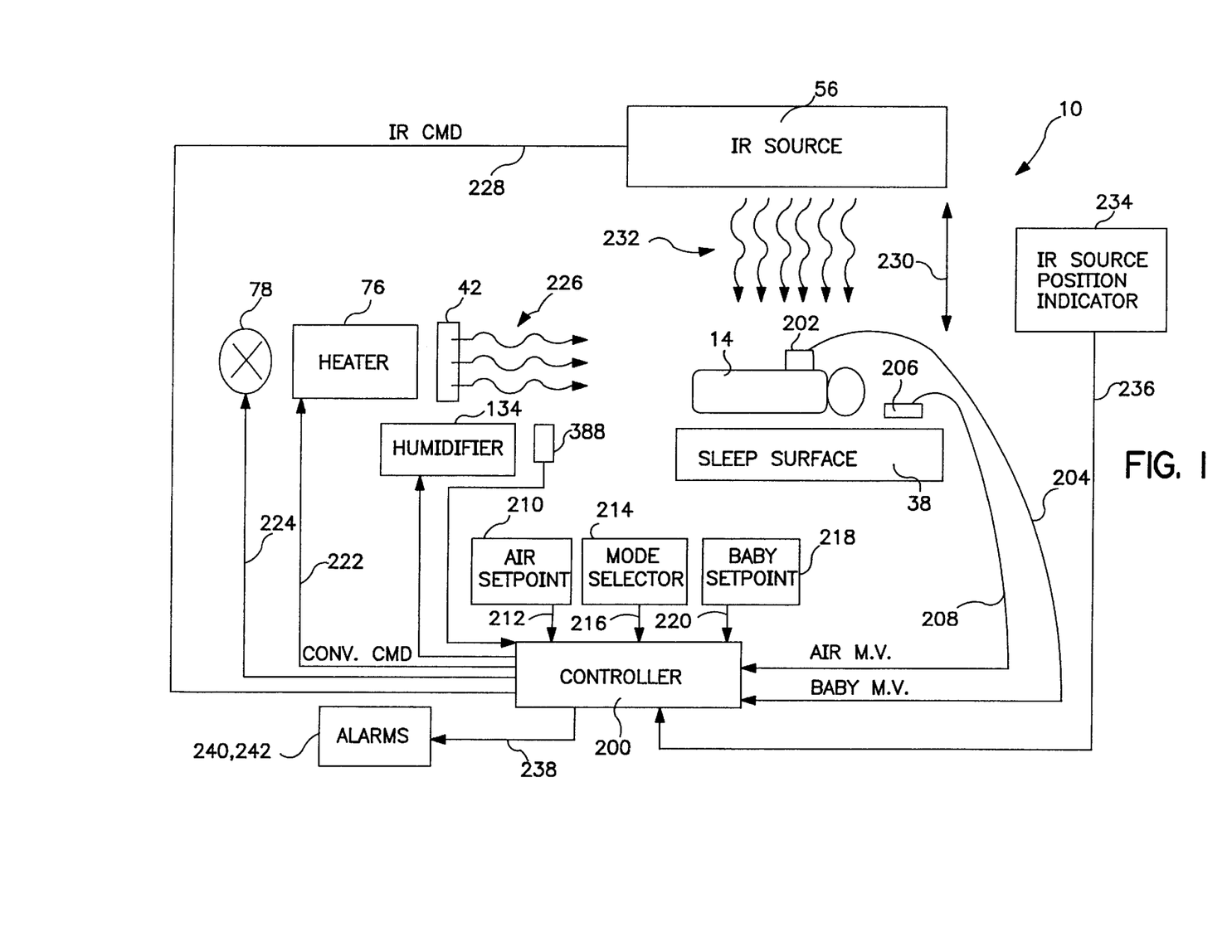
FIG. 1 is a block diagram illustrating a controller for controlling operation of a convective heater and a radiant heater to warm the infant on the sleep surface.

FIG. 1 illustrates a control system for the infant thermal support device 10. FIG. 1 illustrates the infant support portion or sleep surface 38, a convection heater 76, a radiant heater 56, a humidifier 134, and a controller 200. The sleep surface 38 is designed to support an infant or baby 14 in such a position so that either the convection heater 76 or the radiant heater 56 can heat the baby 14 as discussed above. The baby 14 can also be warmed by a combination of the convection heater 76 and radiant heater 56. The convection heater 76 and the radiant heater 56 can be used to warm the baby 14 either directly or indirectly.

Although the terms "baby" and "infant" are used in this specification, is understood that any patient can use the present apparatus of the present invention, not just a baby or infant. Details of the mechanical structure and features of the infant thermal support device 10 are described in copending U.S. patent application Ser. No. 08/532,963 field Sep. 25, 1995, the disclosure of which is hereby expressly incorporated by reference into the present application.

Controller 200 is a microprocessor based controller having an internal memory. The controller 200 receives various inputs. A baby temperature probe or sensor 202 is attached to the baby 14 to provide a measured baby temperature output signal to the controller 200 on line 204. In addition, an air temperature probe or sensor 206 is positioned near the baby 14 to provide a measured air temperature output signal. The air temperature sensor 206 is connected to the controller 200 by line 208.

An air temperature set point input device 210 is coupled to controller 200 by line 212. The air temperature input device allows a caregiver to set a desired air temperature setpoint. A mode selector 214 is also coupled to controller 200 by line 216. Mode selector 214 permits a caregiver to select between a Baby Mode of operation, an Air Mode of operation, and a Procedure Mode of operation for the device 10 as discussed in detail below. A baby temperature set point input device 218 is coupled to controller 200 by line 220. The baby temperature input device 218 permits a caregiver to select the desired temperature for the baby 14.

An output from controller 200 on line 222 is coupled to convective heater 76. Another output of controller 200 is coupled to fan 78 by line 224. Controller 200 therefore controls heater 76 and fan 78 to supply a correct amount of convective heat to the infant thermal support device 10 to warm the baby 14 as illustrated diagrammatically by arrows 226. Air flow is controlled by a plurality of vents 42. Vents 42 direct air to warm the baby 14 and also direct air to form one or more air curtains to provide a controlled patient space.

Another output of controller 200 on line 228 is coupled to radiant heater 56. Therefore, controller 200 controls the IR output from radiant heater 56. The position of radiant heater 56 is adjustable in the direction of double-headed arrow 230 relative to sleep surface 38 by adjusting the canopy support arm (not shown). Heater 56 emits infrared radiation as illustrated diagrammatically by arrows 232 to warm the baby 14. The intensity of radiant heater 56 is adjusted by controller 200 depending upon the position of the heater 56 relative to the sleep surface. A potentiometer or other position indicator 234 is provided to generate an output signal indicative of the position of the radiant heater 56 relative to sleep surface 38. An output of position indicator 234 is coupled to controller 200 by line 236. Controller 200 therefore adjusts the output of radiant heater 56 based on the output signal from position indicator 234 on line 236.

An output from controller 200 on line 238 is coupled to an audible alarm 240 and/or an alarm light 242. Alarms 240 and 242 are used to alert a caregiver of various situations as discussed below.

An output from controller 200 also controls or adjusts the humidifier 134 to control the amount of moisture in the air supplied by the convective heater and used to generate the air curtains. As discussed below, a humidity sensor 388 provides an output signal indicative of the detected relative humidity in the air adjacent sleep surface 38. The controller 200 uses the output signal from humidity sensor 388 to control humidifier 134 to maintain the relative humidity at substantially a preselected level. Also as discussed below, an input device is used to permit the caregiver to adjust the preselected humidity level.

Figure 2:
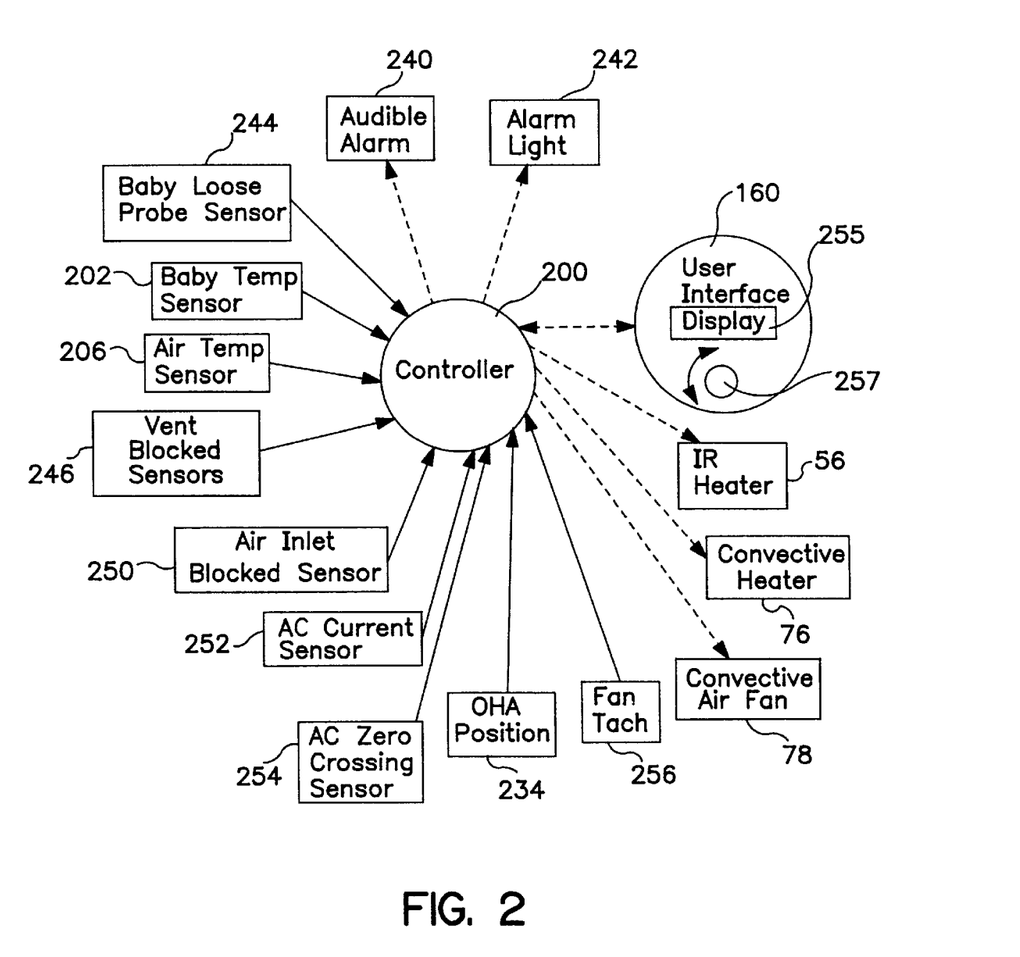
FIG. 2 is a data flow diagram between the controller, a user interface, and the remaining components of the infant thermal support device of the present invention.

FIG. 2 illustrates a data flow block diagram for the controller 200 of the present invention. In addition to the items discussed above, a sensor 244 is provided to indicate that the temperature sensor 202 has come loose from baby 14. A loose probe signal from sensor 244 causes controller 200 to generate an alarm signal on alarms 240 and 242.

In addition, vent blocked sensors 246 are coupled to controller 200. Sensors 246 illustratively include a right vent blocked sensor, a left vent blocked sensor, a front vent blocked sensor, and a rear vent blocked sensor. An air inlet blocked sensor 250 is also coupled to controller 200. Sensors 246 and 250 provide signals to controller 200 to generate alarms 240 and 242 if the air vents or the air inlet are blocked.

Right vent blocked sensor 246 and left vent blocked sensor 248 detect when air vents adjacent sleep surface 38 are blocked. Sensors 246 and 248 provide an input to controller 200 which generates an output signal on display 255 of user interface of 160 or on alarms 240 or 242. In the preferred embodiment, a pair of sensors are co-located on a narrow material with a low thermal conductivity. For instance, sensors 246 and 248 may be a pair of silicon temperature sensors placed on a thin Kapton ribbon. One of the sensors is operated at a low power level. The other is operated at a moderately high power level, resulting in self-heating of the semi-conductor die and thus an increased temperature indication from the sensor. Air flowing through the vents and across the sensor removes heat and therefore lowers the effective temperature indication. The higher the airflow rate, the more heat is removed. The airflow rate is inversely proportional to the difference of the readings from the two sensors. Therefore, when the temperature difference rises above a predetermined level, an output signal is generated by controller 200 to initiate alarm 240 or alarm 242 or to provide an indication on display 255.

An AC current sensor 252 is also coupled to controller 200. In addition, an AC zero crossing sensor 254 is coupled to controller 200. Sensors 252 and 254 permit controller 200 to monitor current before and after the device 10 is turned on. During an "off" period, controller 200 detects whether the heaters actually turn off. The zero crossing sensor 254 checks operation of current sensor 252 and resets the system if no signal is present. A fan tachometer 256 is coupled to controller 200. Fan tachometer 256 provides an input signal to controller 200 indicative of the fan speed. Controller 200 compares the actual fan speed from fan tachometer 256 to the desired fan speed and adjusts a fan command signal to fan 78 accordingly.

A user interface 160 permits the caregiver to input information into controller 200. The user interface 160 may be separate input devices such as devices 210, 214, and 218. The user interface 160 permits the caregiver to input information to controller 200 related to the operation mode, the air temperature set point, the baby temperature set point, a real time clock, and an alarm silencer. Illustratively, a rotatable control wheel 257 is used to scroll through various menu control options. It is understood that any type of control input device may be used. Controller 200 outputs information related to an alarm code, air temperature, and baby temperature to the user interface 160. User interface 160 includes a display 255 so that control information can be displayed to the caregiver.

The communication between controller 200 and user interface 160 is implemented by a serial interface using a master-slave protocol. The controller 200 is the master, and the user interface 160 is slave. Controller 200 controls a communication link by initiating the message transfer. The controller 200 generates a start condition, the user interface address, the read/write bit indicating whether the message is a transmission to the user interface 160 (write) or a request for a message from the user interface 160 (read). Controller 200 also generates a stop condition which indicates the end of a message. The user interface 160 responds only when a transfer has been initiated by the master controller 200. It is understood that other communication protocols may be used in accordance with the present invention.

The controller 200 of the present invention has three operating modes for controlling warming of the baby 14. These operation modes are a Baby Mode, an Air Mode and a Procedure Mode. In the Air Mode, chamber air is under servo-control. The control point is the air setpoint. The infrared energy source is disabled during Air Mode. In the Baby Mode, the controller 200 combines convective heat and infrared energy to servo-control about the baby temperature setpoint. In the Procedure Mode, infrared energy is supplied at a level set by the caregiver. Chamber air is warmed to a preset level using the convective heater.

In this specification, the term "air setpoint" is a control point temperature for Air Mode. The "baby setpoint" is a control point temperature for Baby Mode. "Measured air temperature" is a calibrated temperature measurement of the ambient air by sensor 206 in the vicinity of the sleep surface 38. "Measured baby temperature" is a calibrated temperature measurement of the probe 202 on the baby. "Overhead arm condition" is an indication of the relative position of the overhead arm supporting radiant heater 56 from position indicator 234. "Convective command" is a value that represents the percent convective heater power. "IR command" is a value that represents the desired power density at the mattress surface. "Stability" or "stable" is when temperature fluctuations of less than 0.3° C. are observed, and these fluctuations are predominately centered about the setpoint.

When power to the device 10 is turned on, two possible states are defined, distinguished by the amount of time that the device 10 has been shut off. A warm-start is initiated if the device has been off for less than 10 minutes. The operating mode, setpoints and other conditions in effect prior to the power loss are restored. Controller 200 then resumes control functions, in the state that it was just prior to the removal of power. The device also includes a Prewarm Mode (Cold-Start). The Prewarm Mode is initiated by controller 200 automatically if the power on occurs more than 10 minutes from the last use of the device. This prewarm mode is intended to assist caregivers in preparing the device for use. The functionality of the prewarm "mode" is that of air-mode with the air setpoint at a default value (e.g. 35° C.). An air mode icon will be illuminated on the display, baby mode and procedure mode icons will be extinguished. The message "prewarm" will be indicated on the LCD display screen. Under temperature alarms are inactive in Prewarm mode. Alarms related to system errors (e.g. system failure, heater fault, etc.) are active. When the temperature has reached the Prewarm temperature and has been stable for 2 minutes, the message "Ready for Use— Select Operating Mode" appears on the LCD screen. This message stays on the LCD screen until the mode is canceled. The Prewarm mode is canceled by deliberate action from the caregiver. This can come at any time during the Prewarm mode. Pressing the mode, increment or decrement keys, will initiate an exit from Prewarm mode.

In Air Mode, the air temperature inside the infant receiving space is controlled using only the convective heater 76 and fan 78. The controller 200 adjusts the convective heater 76 to maintain the desired air temperature. In the Air Mode, the radiant heater 56 is off. The baby probe 202 is not needed for operation in the Air Mode. If, however, the probe 202 is connected to the device, then the measured baby temperature is displayed. The baby temperature setpoint is not used in Air Mode. An air icon is illuminated, and Baby Mode and Procedure Mode icons are extinguished. Alarms related to system errors (e.g. system failure, heater fault, etc.) are active.

An "overtemperature condition" exists when the air temperature measured by sensor 206 exceeds the air setpoint by more than 1° C. Overtemperature alarms are always active. An "undertemperature condition" exists when the air temperature measured by sensor 206 is less than the air setpoint by more than 1° C. Undertemperature alarms are active after an undertemperature hold-off period. When the air setpoint is increased, the undertemperature alarm is defeated until the air temperature has risen and stabilized about the new setpoint. After the air temperature has been stable for two minutes at the new setpoint, then undertemperature alarm is reactivated.

A setpoint error ($E_{sp}$) is continuously calculated by the controller 200 from the difference of the air setpoint ($SP_{air}$) and the air temperature measured value as follows:

$$E_{sp} = SP_{air} - MV_{air}$$

Where:

$SP_{air}$ is air temperature setpoint.

$MV_{air}$ is the measured value of the air temperature by sensor 206.

Controller 200 operates to drive $E_{sp}$ to zero. This is accomplished with "three term" control, providing Proportional (P), Integral (I) and Derivative (D) responses, calculated from the present and recent values of $E_{sp}$. The individual responses are summed, forming the input to a power output block (the term block is used here to represent a function or group of functions). The power block receives the PID sum and produces an output command which represents the required amount of heater power to drive $E_{sp}$ toward zero.

Figure 3:
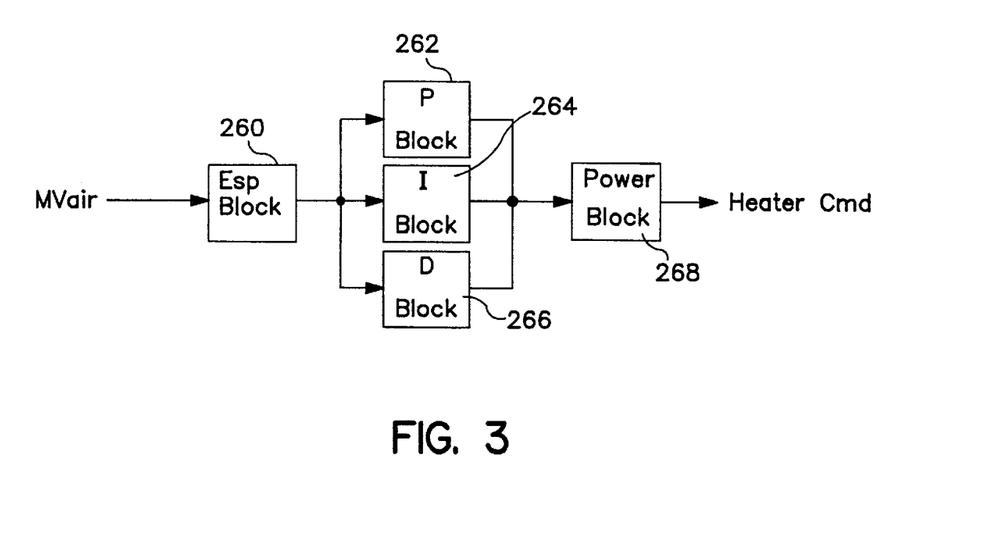
FIG. 3 is a control block diagram for an Air Mode of operation of the present invention.

A block diagram of Air Mode control is illustrated in FIG. 3. The $E_{sp}$ block 260 calculates $E_{sp}$ as discussed above. The P Block 262 in FIG. 3 produces the proportional term which increases with the magnitude of $E_{sp}$, has the same algebraic sign as $E_{sp}$, and is zero when $E_{sp}$ is zero. Calculation of the P term is as follows:

$$P = K_p \cdot E_{sp}$$

Where:

$K_p$ is a proportional gain constant.

The I Block 264 in FIG. 3 produces the integral term which is created from calculation of the area of the curve of $E_{sp}$ vs. time. With constant error, I ramps. When the error is zero, I remains unchanged. An appropriate numerical method (for example the trapezoidal rule) can be used to compute the integral term. The I term is calculated as follows:

$$I = K_i \cdot \int E_{sp} dt$$

Where:

t is time $K_i$ is an integral gain term.

The D Block 266 of FIG. 3 produces the derivative term which is created from calculation of the rate of change $E_{sp}$. With constant error, D is zero. The D term is calculated as follows:

$$D = K_d \cdot \frac{dE_{sp}}{dt}$$

Where:

$K_d$ is a derivative gain term.

P, I and D are added together and presented to the power block 268. The power block translates this sum into a heater command to control convective heater 76. Prior to summation the P, I & D terms are bounded to assure that the heater response is constrained to reasonable values.

Constraint on P: $-P_{max} < P < P_{max}$
Constraint on I: $-I_{max} < I < I_{max}$
Constraint on D: $-D_{max} < D < D_{max}$ Where:

$P_{max}$ is the Lower/Upper limit for P.

$I_{max}$ is the Lower/Upper limit for I.

$D_{max}$ is the Lower/Upper limit for D.

The equation for heater power command is as follows:

$$H_{cmd} = (P + I + D) \bullet K_{htr}$$

Where:

P, I and D are the bound values of above equations.

$K_{htr}$ is a heater gain constant.

Figure 4:
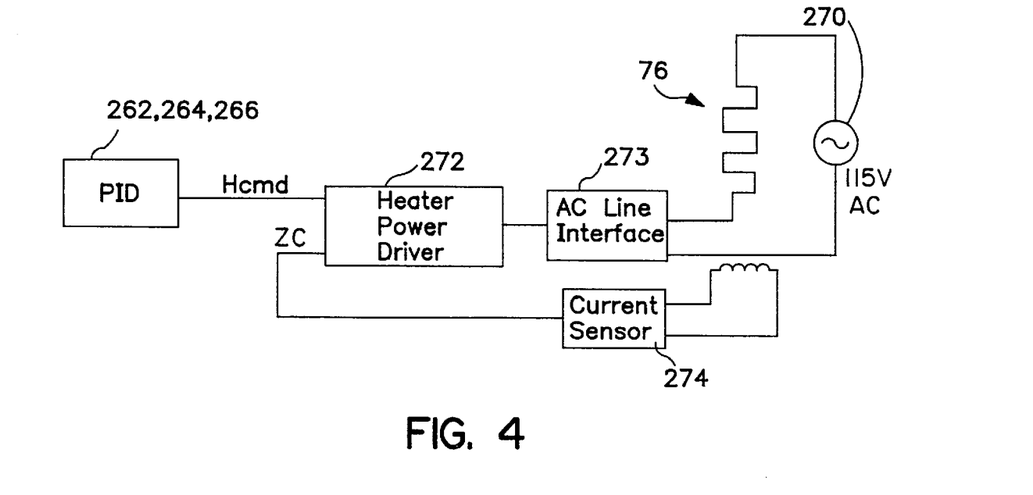
FIG. 4 is a block diagram of a heater control circuit.

A function, the heater power driver, provides power to the heater 76. The input to this function is $H_{cmd}$, which is periodically updated by the PID action. A block diagram of the heater circuit is illustrated in FIG. 4. The heater load 76 is driven from an AC line 270, and is modulated with a time proportioning algorithm. At any given time, the heater 76 is either on or off. Variable power levels are achieved by modulating the on/off characteristic of heater 76. The minimum on time is one-half of the AC line period (e.g. 8.3/10.0 ms with 60/50 Hz mains). The integration period is 100 such half-line cycles. The integration period is chosen so that the time constant of the heater is much greater than integration period. 40% power, for example, is achieved by turning the heater full on for 40 half-cycles and off for 60 half-cycles. At the end of an integration period, a new $H_{cmd}$ is received and a new on/off characteristic is created for the new value of $H_{cmd}$. $H_{cmd}$ signals are created in the PID function block 262, 264, 266 and made available to the heater power driver 272. These two functions operate asynchronously. $H_{cmd}$ is transferred via a mailbox. An AC line interface 273 is coupled between heater power driver 272 and heater 76.

An example output is:

1. Turn on the heater at the start of an integration cycle.
2. Keep it on for the requested power level.
3. Turn the heater off and wait for the integration period to be done.

Power limiting may be desired to keep from exceeding the maximum power draw. A current sensor 274 on the AC lines are available for this.

Figure 5:
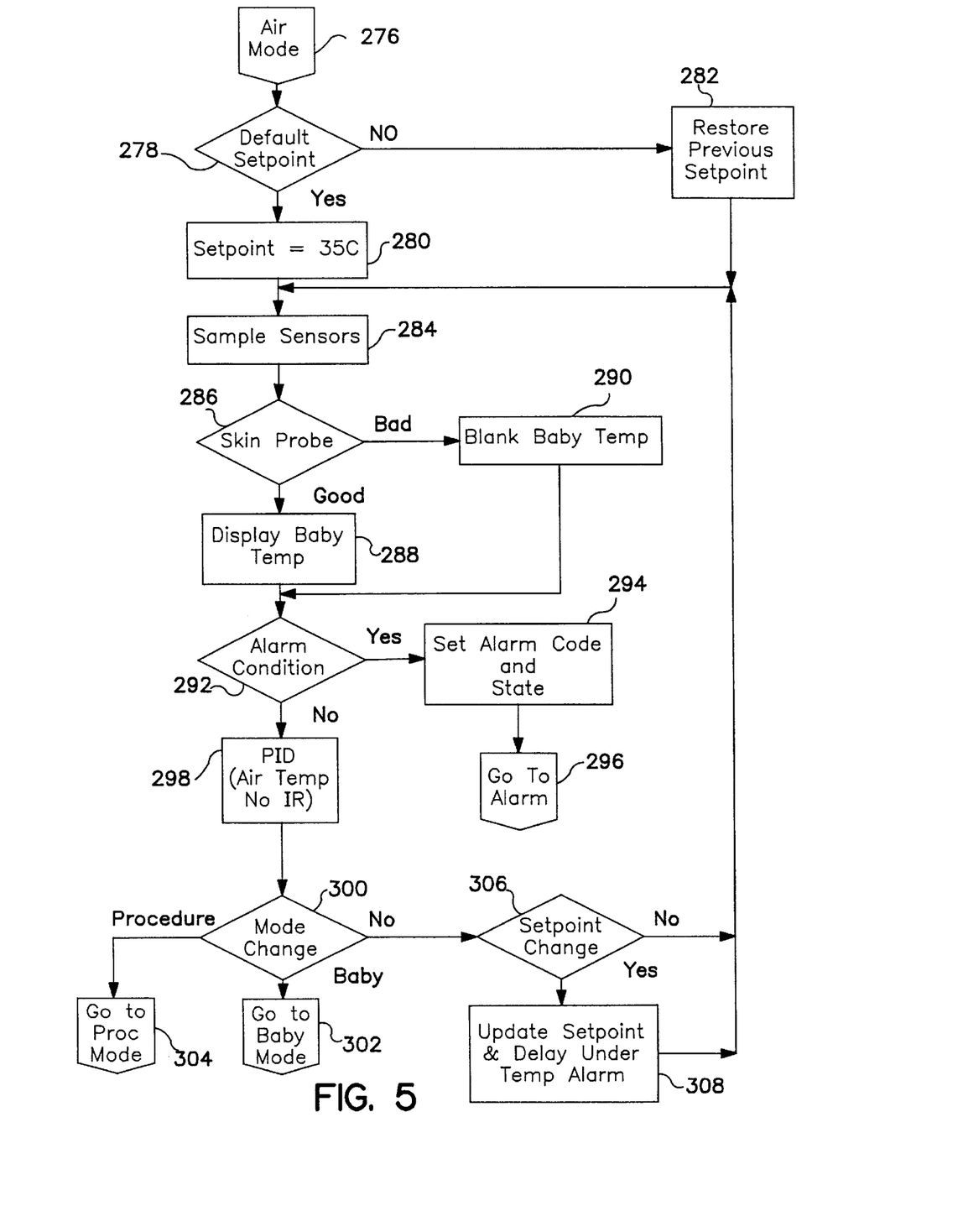
FIG. 5 is a flow chart illustrating the steps performed by the controller during an Air Mode of operation.

FIG. 5 illustrates the steps performed by the controller 200 during the Air Mode of operation. The Air Mode is initiated as illustrated as block 276. Controller 200 determines whether to use the default temperature setpoint at block 278. If the default is to be used, the air temperature setpoint is set at 35° C. as illustrated at block 280. If the default setpoint is not to be used at block 278, controller 200 restores the previous setpoint established by air temperature setpoint input device 210. This step is illustrated at block 282. Once the previous setpoint is restored at block 282, controller advances to block 284 and samples sensors 202 and 206. Controller 200 determines whether the skin probe 202 is connected at block 286. If so, controller 200 display the baby temperature on the display as illustrated at block 288. If the baby temperature sensor 202 is not connected, controller 200 blanks the baby temperature display as illustrated at block 290.

Controller 200 next determines whether an alarm condition exists as illustrated at block 292. If so, the controller 200 sets the alarm code at block 294 and sounds the appropriate alarm 240 or 242 as illustrated at block 296. If an alarm condition does not exist at block 292, the controller 200 uses the PID control discussed above to control the air temperature of the device as illustrated at block 298. Controller 200 then determines whether a mode change has been made on mode selector input 214 at block 300. If a mode change has occurred, controller 200 moves to either the Baby Mode as illustrated at block 302 or the Procedure Mode as illustrated at block 304.

If a mode change has not occurred at block 300, controller 200 determines whether the air temperature setpoint has been changed at block 206. If not, the controller advances back to block 284. If the air temperature setpoint has been changed at block 306, controller 200 updates the setpoint temperature and initiates the delay for the under temperature alarm as discussed above as illustrated at block 308. Controller 200 then advances back to block 284.

In the Baby Mode, controller 200 makes the full use of both heater systems, applying convective heat from heater 76 and also applying radiant warming from heater 56 as needed to maintain the skin temperature of the baby 14 at the baby temperature setpoint. Baby Mode requires that the skin probe 202 is connected to the baby 14. In Baby Mode, the air temperature is displayed, but the air temperature setpoint is not used. A baby icon is illuminated on the display, and the Air and Procedure mode icons are extinguished. An overtemperature condition exists when the baby temperature exceeds the baby temperature setpoint by more than 0.5° C. Overtemperature alarms are always active. An undertemperature alarm exists when the air temperature is less than the baby temperature setpoint by more than 0.5° C. Undertemperature alarms are active after the undertemperature hold-off period. See the discussion in the preceding section (Air Mode) for a definition of undertemperature hold-off.

The setpoint error ($E_{sp}$) for Baby Mode is continuously calculated from the difference of the baby setpoint ($SP_{baby}$) and the baby temperature measured value as follows:

$$E_{sp}=SP_{baby}-MV_{baby}$$

Where:

$SP_{baby}$ is the Baby temperature setpoint.

$MV_{baby}$ is the measured value of the baby.

Figure 6:
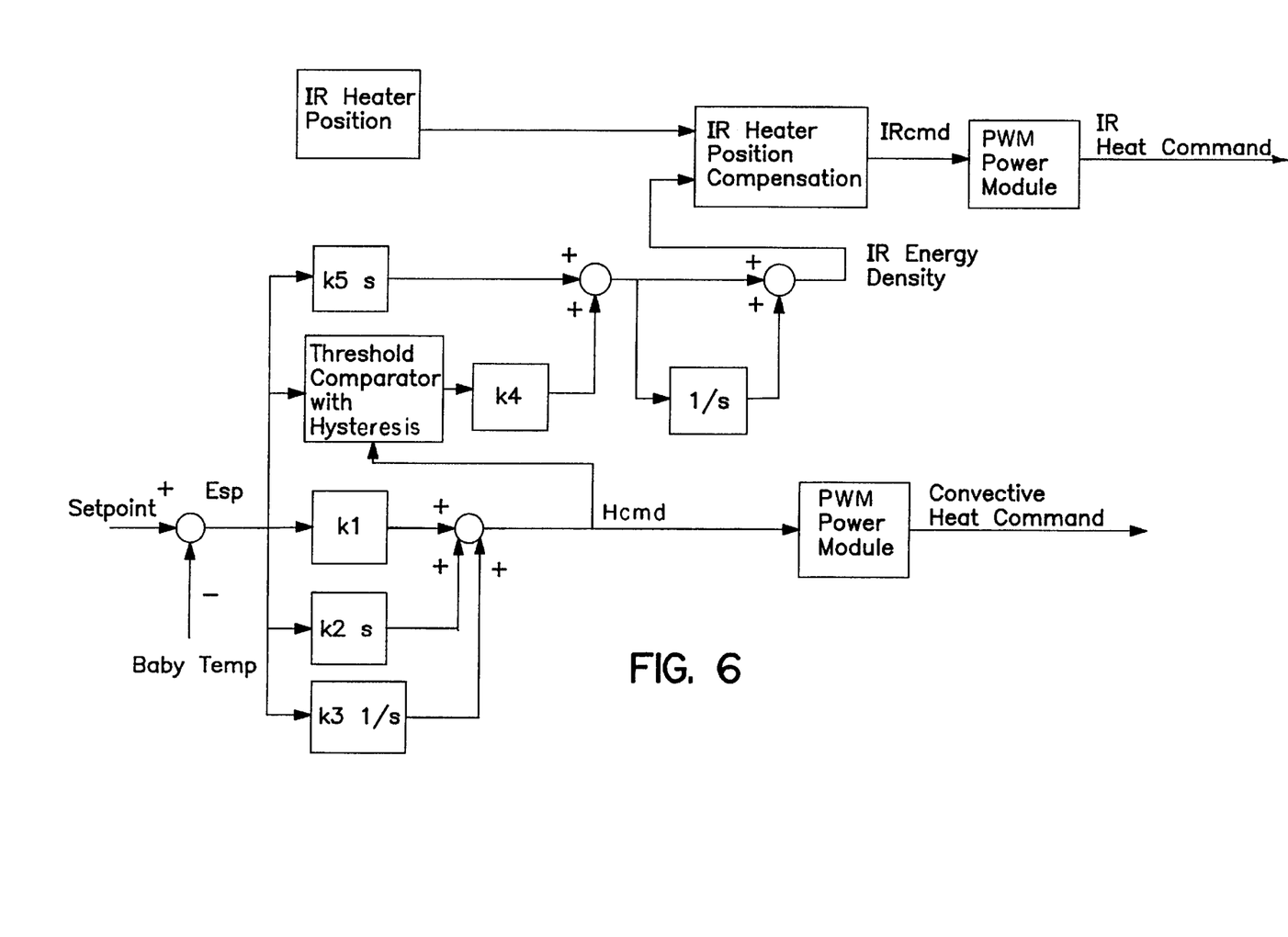
FIG. 6 is a control block diagram of the controller of the present invention.

The convective heater is controlled with the PID control block, as illustrated in FIG. 6. An additional loop, controlling the IR heater is added when operating in the Baby Mode. IR heating is basically an "I" only controller. The IR heating loop derives input from the derivative and heat command ($H_{cmd}$) terms of the convective PID loop.

In FIG. 6, K1 is a convective proportional gain constant. K2 is a convective derivative gain constant. K3 is a convective integral gain constant. K4 is an IR proportional gain constant. K5 is an IR derivative gain constant. The control block diagram is used to generate both the convective heat command for controlling heater 76 and the IR heat command for controlling the radiant heater 56. Both the heat commands are generated by a pulse width modulation power module. The output of the Threshold Comparator is $E_{sp}$ when $H_{cmd}$ is greater than $H_{ul}$. The output of Threshold Comparator is zero when $H_{cmd}$ is between $H_{ul}$ and $H_{ll}$. The output of Threshold Comparator is $-E_{sp}$ when $H_{cmd}$ is less than $H_{ll}$.

Figure 7:
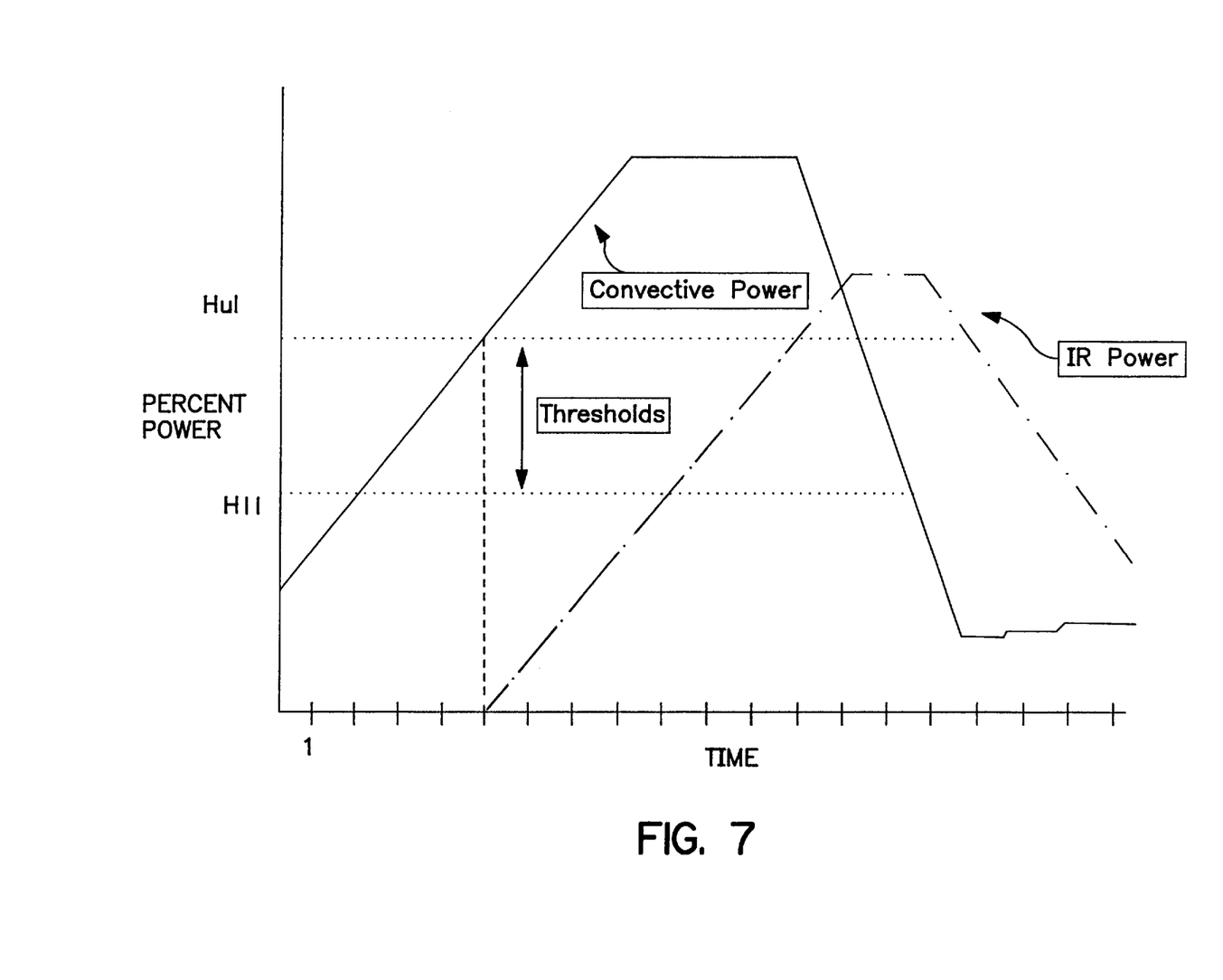
FIG. 7 is a diagrammatic view illustrating control of the convective heater and radiant heater in a Baby Mode of operation.

The derivative term of the convective loop is responsive to the instantaneous rate of change of $E_{sp}$. This provides quick IR heating if the baby measured value ($MV_{baby}$) drops. The $H_{cmd}$ term of the convective loop represents power applied to the convective heater. When convective power exceeds an upper threshold ($H_{ul}$), IR energy begins to ramp up. This continues while the convective power is above $H_{ul}$. When the convective power fails below a lower threshold ($H_{ll}$), the IR energy begins to ramp down. This is illustrated in FIG. 7.

$$IR_{ed(k)} = IR_{ed(k-1)} + \left( K_{ird} \cdot \frac{dE_{sp}}{dt} + SGN \cdot K_{irp} \right) \cdot UR$$

Where:

$IR_{ed(k)}$ and $IR_{ed(k-1)}$ are IR energy densities (e.g. $mW/cm^2$).

$K_{ird}$ is an IR gain constant for the derivative term.

$K_{irp}$ is an IR gain constant for the proportional term.

UR is an update rate of $IR_{ed}$.

SGN is +1 when $H_{cmd}>H_{ul}$, −1 when $Hd_{cmd}<H_{ll}$, and 0 otherwise.

Energy density varies inversely with the distance of the IR heater 56 from the sleep surface 38. Wide variations in energy density (at the sleep surface 38) will be observed for a given power level as the radiant heater is moved up and down. To overcome this, the power level is adjusted as a function of the overhead arm height. A position indicator 234 such as a potentiometer is connected to the arm lift mechanism provides position output signal to controller 200. The potentiometer voltage is periodically monitored by the controller 200 and used in the heater control function. The potentiometer voltage ranges from $V_{posl}$ to $V_{posh}$, and varies directly with position. The relative position is given by:

$$OHA_{rel} = \frac{\Delta V}{Span} = \frac{Vpos - Vposl}{Vposh - Vposl} \cdot 100\%$$

Where:

$V_{pos}$ is the Position Sensor 234 A/D value.

$V_{posl}$ is a Lower limit on the position A/D value.

$V_{posh}$ is an Upper limit on the position A/D value.

$OHA_{rel}$ is the Overhead arm relative position.

The absolute position of the IR sources with respect to the mattress surface is:

$$OHA_{abs}=OHA_{rel}+OHA_{min}$$

Where:

$OHA_{real}$ is the Relative position of the Overhead Arm.

$OHA_{min}$ is the Position of the Overhead Arm when "full down".

To achieve a relatively constant energy density on the mattress surface 38, the following equation is used:

$$IR_{ed} = \frac{1}{K_{ir} \cdot OHA_{abs}^n} \cdot IR_{cmd}$$

Where:

$IR_{ed}$ is the Energy Density at the mattress surface.

$K_{ir}$ is a constant.

$OHA_{abs}$ is the absolute position of the IR sources wrt to the mattress surface as given in the above equation.

n is a constant.

$IR_{cmd}$ is the duty cycle of the IR heater 56.

This constant energy density equation can be rearranged to yield the IR source duty cycle as a function of Energy Density.

$$IR_{cmd}=IR_{ed} \bullet K_{ir} \bullet OHA_{abs}{}^n$$

Modifiers to the control algorithm are necessary to accommodate special conditions. The power command to the heater must be modifiable based on the state of various alarms and system failures. For example if a system failure were to occur, the heater should be commanded to zero power. Power limiting may be necessary to keep from exceeding the maximum power draw. Current sensors on the AC lines are available for this.

Figure 8:
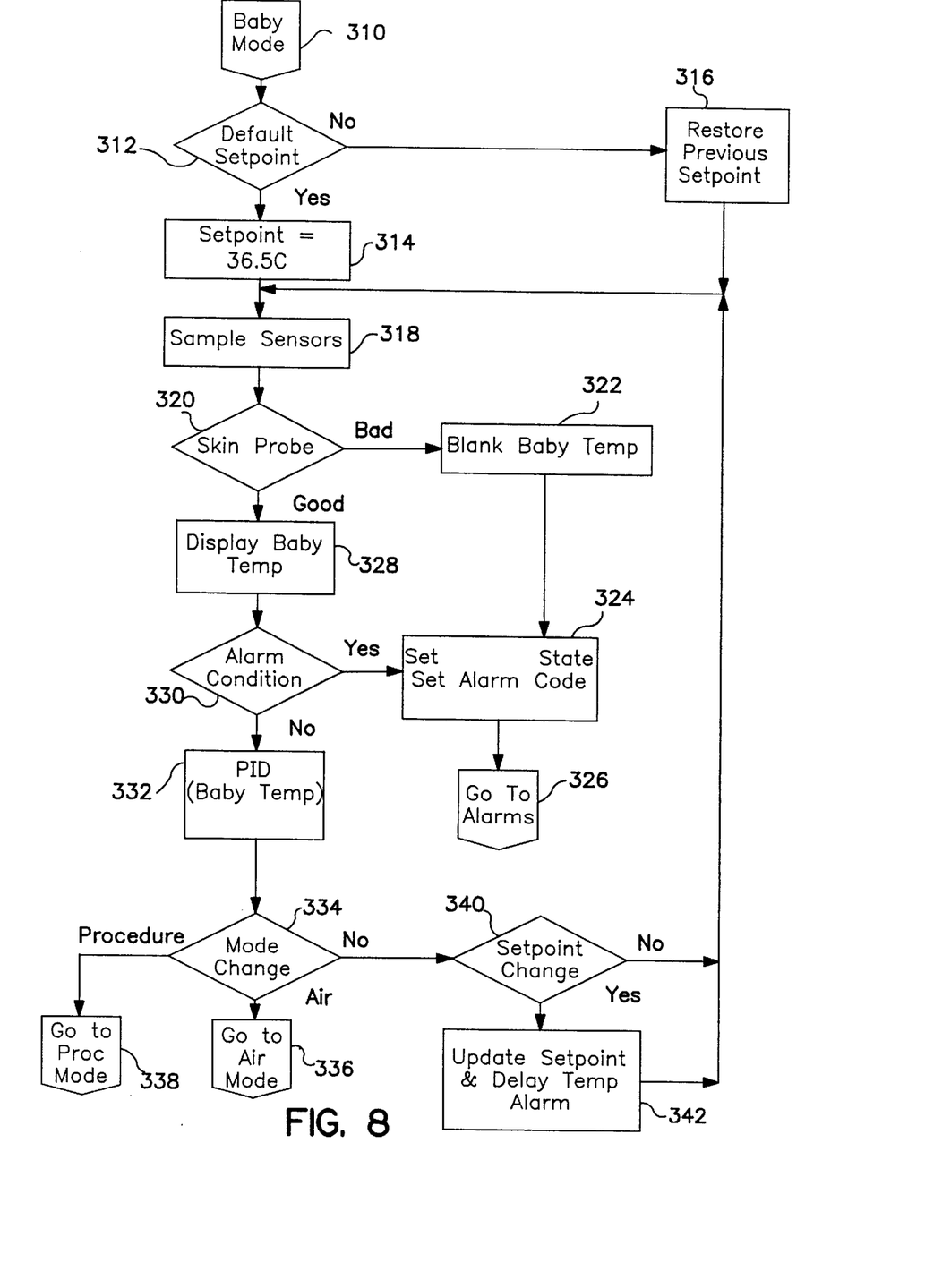
FIG. 8 is a flow chart illustrating the steps performed by the controller during the Baby Mode of operation.

Operation of the controller 200 in the Baby Mode is illustrated in FIG. 8. The Baby Mode begins at block 310. Controller 200 determines whether the use the default baby temperature setpoint as illustrated at block 312. If the default baby temperature setpoint is to be used, controller 200 sets the baby temperature setpoint at 36.5° C. as illustrated at block 314. If the default setpoint is not used, the controller 200 restores the previous baby temperature setpoint input on the baby temperature setpoint input device 218 as illustrated at block 316. The controller 200 then advances to block 318 and samples the output signals from sensors 202 and 206. Controller 200 determines whether skin probe sensor 202 is working or attached at block 320. If not, controller 200 blanks the baby temperature output on the display as illustrated at block 322. Controller then sets an acceptable state and sets an alarm code at block 324. An appropriate alarm 240 or 242 is activated to indicate that the baby sensor 202 is unattached or not functioning as illustrated at block 326. If the baby temperature sensor 202 is functioning properly, controller 200 displays the baby temperature at block 328.

Controller 200 determines whether an alarm condition has occurred at block 330. If so, controller 200 advances to blocks 324 and 326. If an alarm condition has not occurred, controller 200 controls the convective heater 76 and radiant heater 56 using the PID control discussed above as illustrated at block 332.

Controller 200 then determines whether a mode change has occurred at block 334. If so, the controller 200 moves to the Air Mode as illustrated at block 336 or the Procedure Mode as illustrated at block 338.

If the mode is not changed at block 334, controller 200 determines whether the baby temperature setpoint has been changed at block 340. If not, controller 200 advances to block 318. If the baby temperature setpoint has changed at block 340, controller 200 updates the baby temperature setpoint and delays the temperature alarm as illustrated at block 342. Controller 200 then advances to block 318.

Procedure mode is similar to the manual mode of radiant warmers. Caregivers can adjust the IR energy as required by the procedure. The skin probe 202 need not be connected in this mode. If it is, the skin temperature will be displayed. If it is not, the skin temperature on the display will be blanked.

The air temperature is displayed, but the air temperature setpoint is extinguished. The procedure icon is illuminated, and the air and baby icons are extinguished. IR energy density is set by the caregiver. The IR source duty cycle is modulated as a function of the overhead arm distance, as described above. The convective energy is supplied at a specified level.

Figure 9:
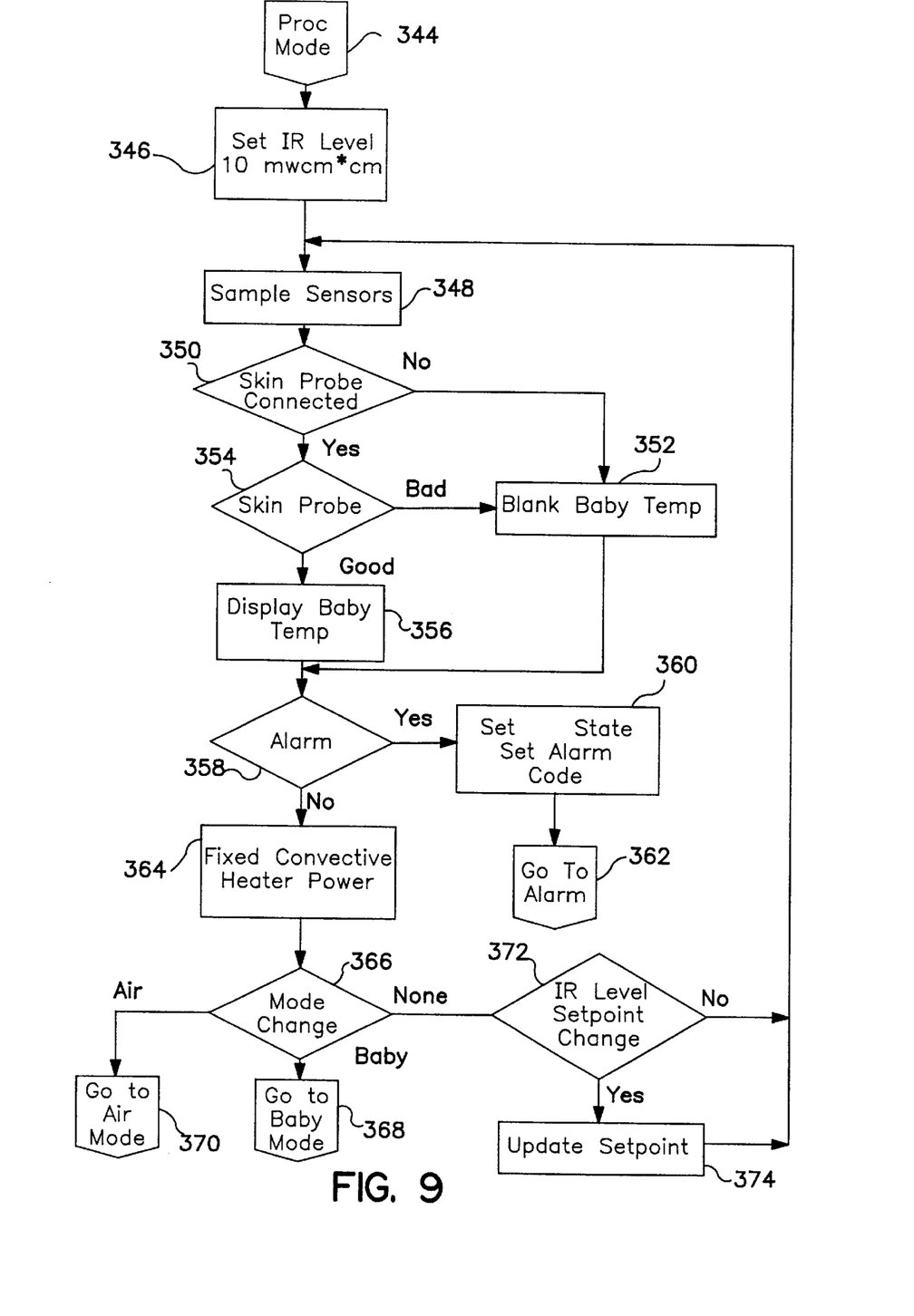
FIG. 9 is a flow chart illustrating the steps performed by the controller of the present invention during a Procedure Mode of operation.

The operation of controller 200 in the Procedure Mode is illustrated in FIG. 9. The Procedure Mode begins at block 344. Controller 200 sets the IR level at 10 mW/cm$^2$ as illustrated at block 346. Controller 200 samples sensors 202 and 206 as illustrated at block 348. Controller 200 determines whether the baby skin probe is connected at block 350. If not, controller 200 blanks the baby temperature output to the display as illustrated at block 352. Controller 200 then advances to block 358. If the skin probe is connected at block 350, controller determines whether the output from the skin probe is a valid reading at block 354. If not, controller 200 advances to block 352. If the sensor 202 reading is valid, controller 200 display the baby temperature at block 356.

Controller 200 determines whether an alarm condition is present at block 358. If so, controller 200 sets a acceptable state and sets the alarm code at block 360. Controller 200 then sounds the appropriate alarm 240 or 242 as illustrated at block 362. If an alarm condition is not present at block 358, controller 200 provides a fixed convective heater power as illustrated at block 364. Controller 200 then determines whether a mode change has occurred from mode selector 214 as illustrated at block 366. If a mode change has occurred, controller 200 advances to the Baby Mode as illustrated at block 368 or the Air Mode as illustrated at block 370.

If the mode has not changed at block 366, controller 200 determines whether the IR level setpoint has changed at block 372. If not, controller 200 advances to block 348. If the IR level setpoint has changed at block 372, controller 200 updates this setpoint as illustrated at block 374 and then advances to block 348.

Figure 10:
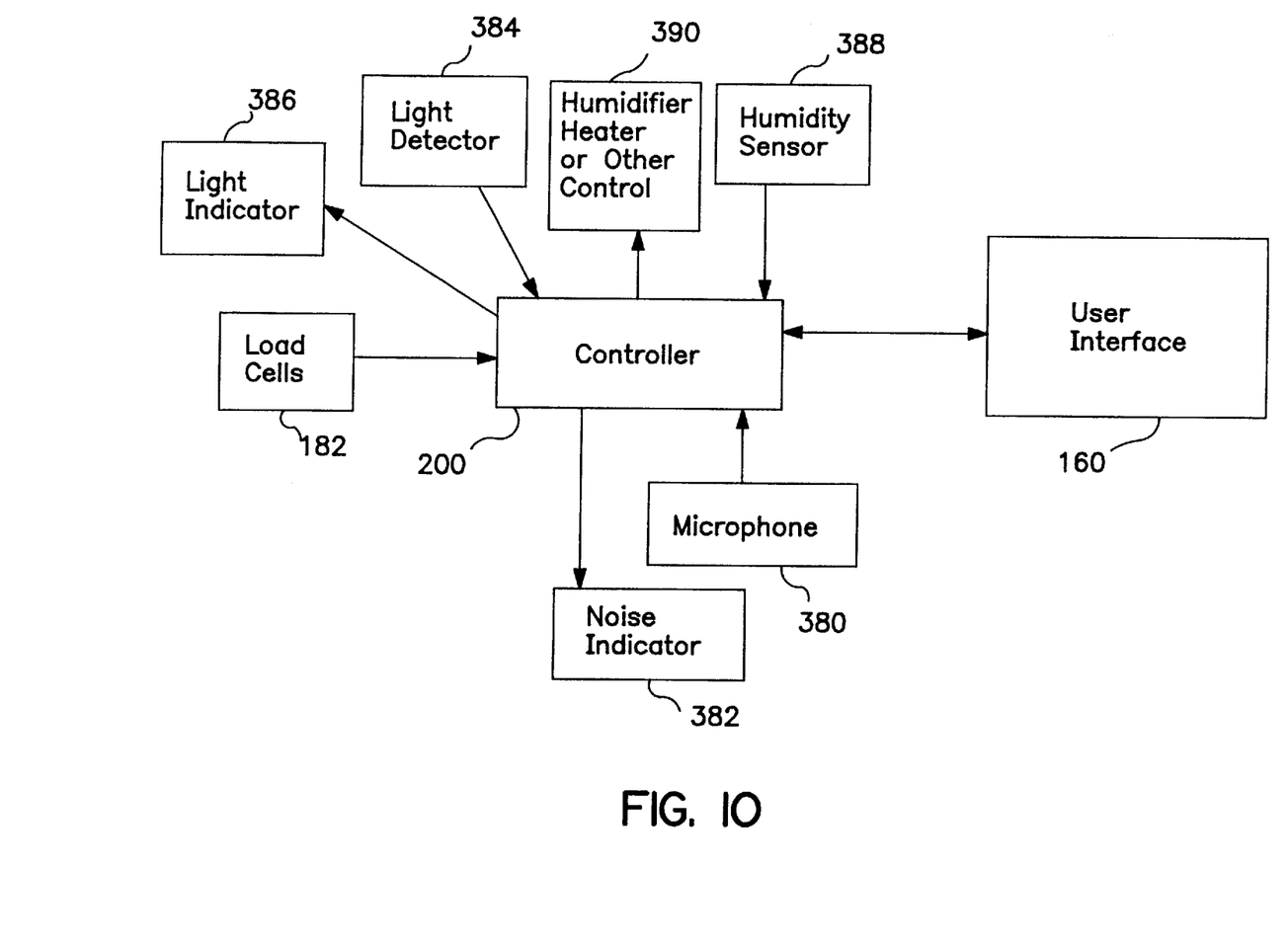
FIG. 10 is a block diagram illustrating additional features of the present invention.

Additional features of the present invention are illustrated in FIG. 10. Another aspect of the present invention is noise monitoring in the region adjacent the device 10. The noise monitor apparatus provides a visual indication using display 255 or alarm light 242 when a predetermined noise threshold has been exceeded. A microphone 380 is located in close proximity to device 10. The microphone 380 may be positioned on the device 10 itself near sleep surface 38. In addition, microphone 380 may be placed on the baby 14 along with temperature sensor 202. The microphone provides an output signal to controller 200 to indicate the noise level. A caregiver can set a predetermined threshold level using a control on user interface 160. If the predetermined threshold noise level is exceeded, controller 200 generates an output signal to initiate the noise indicator 382.

Controller 200 is also coupled to a light detector 384. Again, light detector 384 can be located anywhere adjacent device 10. Preferably, light detector 384 is located near sleep surface 38. Light detector 384 may be coupled to the baby 14 adjacent temperature sensor 202. The caregiver can provide a predetermined threshold light level using user interface device 160. Controller 200 provides an output signal to a light indicator 386 indicating that the preselected light level has been exceeded. A display 255 on the user interface 160 can be used for the light indicator.

Controller 200 can store the signals from microphone 380 and light detector 384 if desired. These stored signals can be processed and displayed to the caregiver. The noise indicator 382 and light indicator 386 may be coupled to the device 10 or located at a remote location.

Controller 200 is also coupled to an output from load cells 182. Controller 200 processes the signals from load cells 182 to provide an indication of the weight of the patient. The output may be displayed on display 255 of user interface 160. A caregiver can provide an input for a weight request or tare weight request to the scale using controls on user interface 160. Controller 200 then measures the weight and provides the weight indication signal to user interface 160. If desired, the weight signal can be transmitted to remote location. The scale works even when the sleep surface 38 is aligned at an angled orientation.

The device 10 also includes a humidity sensor 388 for detecting relative humidity. Typically, a humidifier 134 for the patient thermal support device 10 includes an evaporator tray which is heated by a heater to supply water vapor to an air stream. In the present invention, a caregiver can control the desired relative humidity in the air moving through the device 10. Controller 200 detects the humidity level from sensor 388 and compares it to the preset humidity level set by the caregiver or automatically by the controller to a default level. Controller 200 sends an output signal to a humidifier heater or other humidifier control as illustrated at block 390. For instance, if it is desired to increase the humidity, the humidifier heater temperature is increased to increase the level of water vapor in the air. Controller 200 generates output signals to user interface 160 indicating that the humidifier is present, indicating the percent relative humidity, or indicating that the humidifier evaporation tray is out of water. A caregiver can use the user interface 160 to turn on the humidifier and to set the preselected humidity level.

Although a PID controller is disclosed in the illustrated embodiment, it is understood that a controller using another type of control system or technique may be used to control the convective heater 76, the radiant heater 56, and the humidifier 134 in accordance with the present invention. For example, proportional control, adaptive control, fuzzy logic control, or neural network control can be used for controller 200, if desired.

Although the invention has been described with reference to preferred embodiments, additional variations and modifications exist within the scope and spirit of the invention as described and defined in the following claims.

We claim:

1. A patient warming apparatus comprising:
   a support surface for supporting a patient;
   a convective heater;
   a radiant heater; and
   a controller having a first output coupled to the convective heater and a second output coupled to the radiant heater for varying output power and heat levels of the convective heater and the radiant heater, respectively, to maintain the patient located on the support surface at substantially a preselected temperature.

2. The apparatus of claim 1, further comprising a temperature sensor having an output coupled to the controller to provide feedback to the controller.

3. The apparatus of claim 2, further comprising an alarm coupled to the controller, the controller generating an alarm signal if the output from the temperature sensor changes by a predetermined level.

4. The apparatus of claim 1, further comprising a humidifier for adding moisture to air adjacent the support surface.

5. The apparatus of claim 4, further comprising a humidity sensor having an output coupled to the controller, the controller having a third output coupled to the humidifier to adjust the humidifier based on the output from the humidity sensor and to maintain the humidity at substantially a preselected level.

6. The apparatus of claim 1, further comprising an air curtain generator for providing at least one air curtain over the support surface to create a controlled patient space.

7. The apparatus of claim 1, further comprising a canopy and means to move the canopy relative to the support surface between an up position spaced apart from the support surface and a down position located in close proximity to the support surface.

8. The apparatus of claim 7, wherein the radiant heater is mounted on the canopy.

9. The apparatus of claim 8, further comprising a position indicator for generating an output signal related to a distance between the radiant heater and the support surface, the position indicator being coupled to the controller to permit the controller to adjust the output power level of the radiant heater based upon said distance.

10. The apparatus of claim 1, further comprising a temperature sensor configured to be coupled to the patient, the temperature sensor having an output coupled to the controller to provide feedback to the controller.

11. The apparatus of claim 10, further comprising an alarm coupled to the controller, the controller generating an alarm signal if the output from the temperature sensor changes above or below a predetermined level.

12. The apparatus of claim 1, further comprising an input device coupled to the controller to permit a caregiver to adjust the preselected temperature.

13. The apparatus of claim 1, wherein the controller actives only the convective heater until an output power level of the convective heater exceeds an upper limit, at which point the controller activates the radiant heater.

14. The apparatus of claim 13, wherein the controller continues to increase the output power level of the radiant heater until the output power level of the convective heater drops below the upper limit.

15. The apparatus of claim 13, wherein the controller reduces the output power level of the radiant heater when the output power level of the convective heater drops below a lower limit.

16. The apparatus of claim 1, further comprising a noise detector coupled to the controller, the controller generating an output signal to an indicator if noise detected by the noise detector exceeds a preset level.

17. The apparatus of claim 1, further comprising a light detector coupled to the controller, the controller generating an output signal to an indicator if light detected by the light detector exceeds a preset level.

18. The apparatus of claim 1, further comprising a scale coupled to the controller, the controller generating an output signal to a display indicating a weight of the patient on the support surface.

19. An apparatus controlling operation of a patient warming device comprising:
   a support surface for supporting a patient;
   a convective heater for supplying convective heat to warm the patient;
   a radiant heater for supplying radiant heat to warm the patient;
   a humidifier for adding moisture to air adjacent the support surface;
   a control apparatus for the warming device comprising:
      a controller having a first output coupled to the convective heater and a second output coupled to the radiant heater for varying output power and heat levels of the convective heater and the radiant heater, respectively, to maintain the patient located on the support surface at substantially a preselected temperature, the controller having a third output coupled to the humidifier to adjust an output from the humidifier;
      a temperature sensor having an output coupled to the controller to provide feedback to the controller so that the controller maintains the patient located on the support surface at substantially the preselected temperature; and
      a humidity sensor having an output coupled to the controller, the controller adjusting the humidifier based on the output from the humidity sensor to permit the controller to maintain the humidity at substantially a preselected level.

20. The apparatus of claim 19, wherein the warming device further comprises an air curtain generator for providing at least one air curtain over the support surface to create a controlled patient space.

21. The apparatus of claim 19, wherein the warming device further comprises a canopy and means to move the canopy relative to the support surface between an up position spaced apart from the support surface and a down position located in close proximity to the support surface.

22. The apparatus of claim 21, wherein the radiant heater is mounted.

23. The apparatus of claim 22, further comprising a position indicator for generating an output signal related to a distance between the radiant heater and the support surface, the position indicator being coupled to the controller to permit the controller to adjust the output power level of the radiant heater based upon said distance.

24. The apparatus of claim 23, wherein the temperature sensor is configured to be coupled to the patient.

25. The apparatus of claim 19, further comprising an alarm coupled to the controller, the controller generating an alarm signal if the output from the temperature sensor changes above or below a predetermined level.

26. The apparatus of claim 19, further comprising an input device coupled to the controller to permit a caregiver to adjust the preselected temperature and the preselected humidity level.

27. The apparatus of claim 19, further comprising a noise detector coupled to the controller, the controller generating an output signal to an indicator if noise detected by the noise detector exceeds a preset level.

28. The apparatus of claim 19, further comprising a light detector coupled to the controller, the controller generating an output signal to an indicator if light detected by the light detector exceeds a preset level.

29. The apparatus of claim 19, further comprising a scale coupled to the controller, the controller generating an output signal to a display indicating a weight of the patient on the support surface.

* * * * *